United States Patent
Taoka et al.

(10) Patent No.: US 7,666,659 B2
(45) Date of Patent: Feb. 23, 2010

(54) PROCESS FOR PRODUCING OPTICALLY ACTIVE 3-HYDROXYPROPIONIC ESTER DERIVATIVE

(75) Inventors: Naoaki Taoka, Takasago (JP); Daisuke Moriyama, Takasago (JP); Kohei Mori, Takasago (JP); Takahiro Oishi, Takasago (JP)

(73) Assignee: Kaneka Corporation, Osaka (JP)

( * ) Notice: Subject to any disclaimer, the term of this patent is extended or adjusted under 35 U.S.C. 154(b) by 537 days.

(21) Appl. No.: 10/536,768

(22) PCT Filed: Dec. 8, 2003

(86) PCT No.: PCT/JP03/15644

§ 371 (c)(1),
(2), (4) Date: May 27, 2005

(87) PCT Pub. No.: WO2004/052829

PCT Pub. Date: Jun. 24, 2004

(65) Prior Publication Data

US 2006/0166342 A1    Jul. 27, 2006

(30) Foreign Application Priority Data

Dec. 6, 2002    (JP) .............................. 2002-355305
May 12, 2003   (JP) .............................. 2003-133456

(51) Int. Cl.
*C12P 41/00*    (2006.01)
(52) U.S. Cl. ..................................... 435/280
(58) Field of Classification Search ....................... None
See application file for complete search history.

(56) References Cited

U.S. PATENT DOCUMENTS 4,734,367 A * 3/1988 Leuenberger et al. ....... 435/135

FOREIGN PATENT DOCUMENTS

EP        0 212 859 A2     3/1987
JP        03-285689     * 12/1991

OTHER PUBLICATIONS

Barth et al., "Physiology and genetics of the dimorphic fungus Yarrowia lipolytica", FEMS Microbiology Reviews 19 : 219-237 (1997).*
ATCC Bacteria and Bacteriophages, 19th Edition, p. 304 (1996).*
Kido et al., "New Access to dl-Paniculide A Using α-PhenylthioVinylbutenolide as Synthetic Block", Tetrahedron 43 (23) : 5467-5474 (1987).*

* cited by examiner

*Primary Examiner*—Sandra E Saucier
(74) *Attorney, Agent, or Firm*—Sughrue Mion, PLLC

(57) ABSTRACT

The present invention is to provide a process for simply producing an optically active 3-hydroxypropionic ester derivative useful as a medicament intermediate from an inexpensive material. More specifically, the present invention is directed to a process for producing an optically active 3-hydroxypropionic ester derivative comprising reacting an acetic ester derivative available at low cost with a base and a formic ester, thereby converting the acetic ester derivative into a 2-formylacetic ester derivative, and thereafter, stereospecifically reducing the formyl group of the derivative by use of an enzymatic source capable of stereoselectively reducing the formyl group of the derivative.

15 Claims, No Drawings

PROCESS FOR PRODUCING OPTICALLY ACTIVE 3-HYDROXYPROPIONIC ESTER DERIVATIVE

This application is a National Stage of International Application No. PCT/JP2003/015644, filed Dec. 18, 2003.

TECHNICAL FIELD

The present invention relates to a process for producing an optically active 3-hydroxypropionic ester derivative useful as an intermediate for a medicament, in particular, an optically active 2-(hydroxymethyl)-3-phenylpropionic ester derivative.

More particularly, the present invention relates to a process for producing an optically active 3-hydroxypropionic ester derivative, in particular, an optically active 2-(hydroxymethyl)-3-phenylpropionic ester derivative, the process which is characterized by comprising synthesizing a 2-formylacetic ester derivative by using an acetic ester derivative available at low cost, a formic ester and a base, and stereoselectively reducing the 2-formylacetic ester derivative by use of an enzymatic source capable of stereoselectively reducing the formyl group thereof.

BACKGROUND ART

Conventionally, the following processes are known for producing an optically active 3-hydroxypropionic ester derivative.

1) A process for obtaining an optically active 2-substitued-3-hydroxypropionic acid by asymmetrically oxidating 2-substituted-1,3-propanediol by use of a microorganism (Chem. Lett., 1979, Vol. 11, 1379-1380).

2) A process for obtaining an optically active 3-hydroxypropionic ester derivative by reducing a 0.1% 2-formylacetate ester derivative by use of a microorganism belonging to the genus *Candida, Rhodotorula*, or *Torulopsis* (Japanese Patent Laid-Open No. 60-199389).

However, in the process 1), the diol compound used as a substrate is expensive and the stereoselectivity is low in the case where the 2-position has a substituent except for a methyl group. Furthermore, in the process 2), since a substrate in use negatively affects the reducing activity of a microorganism and an enzyme, the concentration of a starting material is extremely low. Both processes have significant problems as an industrial process.

On the other hand, for producing a 2-formylacetic ester derivative, the following processes are known.

3) A process for obtaining ethyl α-(formyl) 2-methyl-1,3-dioxolane-2-propionate by formylating ethyl 2-methyl-1,3-dioxolane-2-propionate with NaH and ethyl formate, followed by subjecting to distillation purification (Phosphorus and Sulfur, 1986, Vol. 28, 330-345).

4) A process for obtaining crude ethyl 2-formylphenylpropionate by formylating ethyl phenylpropionate with a sodium metal and ethyl formate (Eur. J. Med. Chem., 1988 Vol. 23, 53-62).

However, in any one of the processes, a reaction product contains an unreacted starting material and a large amount of impurities such as a mineral oil derived from NaH. Therefore, for obtaining a highly purified product, a purification step using distillation, crystallization or column is required. There are problems mentioned above for putting such a process to an industrial use.

SUMMARY OF THE INVENTION

In view of the aforementioned circumstances, it is an object of the present invention to provide a process for simply producing an optically active 3-hydroxypropionic ester derivative useful as an intermediate for a medicament, in particular, an optically active 2-(hydroxymethyl)-3-phenylpropionic ester derivative, from a raw material easily available at low cost.

The present inventors conducted extensive studies on the aforementioned object and consequently they have found a process for simply producing an optically active 3-hydroxypropionic ester derivative by synthesizing a 2-formylacetic ester derivative at a high purity from an acetic ester derivative available at low cost by a simple process, and stereoselectively reducing the 2-formylacetic ester derivative by use of an enzymatic source capable of stereoselectively reducing the formyl group thereof. Based on the finding, the present invention has been achieved.

According to the present invention, there is provided a process for producing a 2-formylacetic ester derivative represented by the general formula (2):

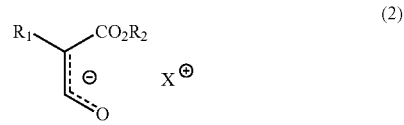

(2)

where $R_1$ represents an alkyl group having 2 to 10 carbon atoms, an optionally substituted aralkyl group having 5 to 15 carbon atoms, or an optionally substituted aryl group having 5 to 15 carbon atoms; $R_2$ represents an alkyl group having 1 to 10 carbon atoms, or an optionally substituted aralkyl group having 5 to 15 carbon atoms; and X represents H, Li, Na or K, characterized by comprising the steps of:

reacting an acetic ester derivative represented by the general formula (1):

(1)

where $R_1$ and $R_2$ are the same as described above, with a base and a formic ester, thereby converting the acetic ester derivative into 2-formylacetic ester derivative represented by the general formula (2); and removing impurities from the reaction mixture into an organic layer formed by addition of an organic solvent and water thereto, while transferring/dissolving the derivative represented by the general formula (2) into a resulting aqueous layer.

According to the present invention, there is also provided a process for producing an optically active 3-hydroxypropionic ester derivative represented by the general formula (3):

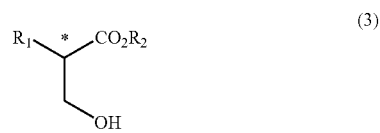

(3)

where $R_1$ and $R_2$ are the same as described in the general formula (1); and * represents an asymmetric carbon atom, characterized by stereoselectively reducing a 2-formylacetic ester derivative represented by the general formula (2):

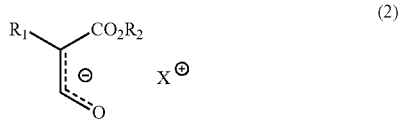

where $R_1$, $R_2$ and X represent the same groups as described above, by use of an enzymatic source capable of stereoselectively reducing the formyl group thereof.

Furthermore, according to the present invention, there is provided an optically active 2-(hydroxymethyl)-3-(3,4-methylenedioxyphenyl)-propionic ester derivative represented by the general formula (4):

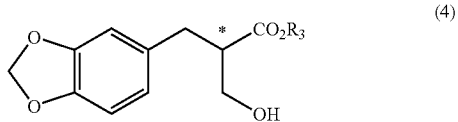

where $R_3$ represents an alkyl group having 1 to 10 carbon atoms; and * represents an asymmetric carbon atom.

Moreover, according to the present invention, there is provided a 2-formylacetic ester derivative represented by the general formula (5):

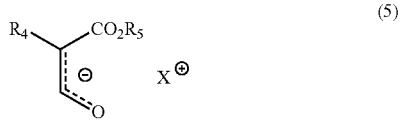

where $R_4$ represents an alkyl group having 2 to 6 carbon atoms; $R_5$ represents an alkyl group having 1 to 10 carbon atoms; and X represents H, Li, Na or K.

DETAILED DESCRIPTION OF THE INVENTION

The present invention will now be described in detail below.

First, compounds involved in the present invention will be described. In the formulas (1), (2) and (3), $R_1$ represents an alkyl group having 2 to 10 carbon atoms, an optionally substituted aralkyl group having 5 to 15 carbon atoms, or an optionally substituted aryl group having 5 to 15 carbon atoms.

Examples of such an alkyl group having 2 to 10 carbon atoms includes ethyl group, n-propyl group, iso-propyl group, n-butyl group, sec-butyl group, tert-butyl group, n-pentyl group, and hexyl group.

Examples of a substituent of such a an optionally substituted aralkyl group having 5 to 15 carbon atoms and an optionally substituted aryl group having 5 to 15 carbon atoms include halogen atoms such as fluorine atom, chlorine atom, and bromine atom; alkyl groups having 1 to 10 carbon atoms such as methyl group and ethyl group; alkoxy groups having 1 to 10 carbon atoms such as methoxy group and ethoxy group; nitro group; cyano group; and methylenedioxy group.

Note that the number of carbon atoms of the aralkyl group and aryl group refers to the number of carbon atoms of the aralkyl group and aryl group alone without including the number of carbon atoms of a substituent.

Examples of such a an optionally substituted aralkyl group having 5 to 15 carbon atoms include benzyl group, o-chlorobenzyl group, m-bromobenzyl group, p-fluorobenzyl group, p-nitrobenzyl group, p-cyanobenzyl group, m-methoxybenzyl group, 3,4-methylenedioxybenzyl group, phenethyl group, naphthylmethyl group, and pyridylmethyl group.

Examples of such an optionally substituted aryl group having 5 to 15 carbon atoms include phenyl group, o-chlorophenyl group, m-bromophenyl group, p-fluorophenyl group, p-nitrophenyl group, p-cyanophenyl group, m-methoxyphenyl group, naphthyl group, pyridyl group, and indolyl group.

Of them, a preferable $R_1$ is an alkyl group having 2 to 10 carbon atoms, and an optionally substituted aralkyl group having 5 to 15 carbon atoms. Examples of such an alkyl group having 2 to 10 carbon atoms include preferably n-propyl group, n-butyl group, and n-pentyl group; and more preferably n-butyl group. Examples of such an optionally substituted aralkyl group having 5 to 15 carbon atoms include preferably benzyl group, and 3,4-methylenedioxy benzyl group; and more preferably 3,4-methylenedioxybenzyl group.

In the formulas (1), (2) and (3), $R_2$ represents an alkyl group having 1 to 10 carbon atoms, or an optionally substituted aralkyl group having 5 to 15 carbon atoms. Examples of a substituent of such an optionally substituted aralkyl group having 5 to 15 carbon atoms, mention may be made of the same groups as exemplified as those for an aralkyl group of $R_1$. The number of carbon atoms of such a substituent is not included in those of an aralkyl group of $R_2$.

Examples of such an alkyl group having 1 to 10 carbon atoms include methyl group, ethyl group, n-propyl group, iso-propyl group, n-butyl group, sec-butyl group, tert-butyl group, n-pentyl group, and hexyl group, and preferably methyl group, ethyl group and tert-butyl group.

Examples of such an optionally substituted aralkyl group having 5 to 15 carbon atoms include a benzyl group, o-chlorobenzyl group, m-bromobenzyl group, p-fluorobenzyl group, p-nitrobenzyl group, p-cyanobenzyl group, m-methoxybenzyl group, 3,4-methylenedioxybenzyl group, phenethyl group, naphthylmethyl group, and pyridylmethyl group; and preferably benzyl group.

Of them, an alkyl group having 1 to 10 carbon atoms is preferable as $R_2$, methyl group and ethyl group are more preferable.

In the formula (4), $R_3$ is an alkyl group having 1 to 10 carbon atoms. Examples of such an alkyl group having 1 to 10 carbon atoms include methyl group, ethyl group, n-propyl group, iso-propyl group, n-butyl group, sec-butyl group, tert-butyl group, n-pentyl group, and hexyl group.

In the formulas (3) and (4), * represents an asymmetric carbon atom.

In the formula (5), $R_4$ is an alkyl group having 2 to 6 carbon atoms. Examples of such an alkyl group having 2 to 6 carbon atoms include ethyl group, n-propyl group, iso-propyl group, n-butyl group, sec-butyl group, tert-butyl group, n-pentyl group, and hexyl group; preferably, n-propyl group, n-butyl group, and n-pentyl group; and more preferably, n-butyl group.

In the formula (5), $R_5$ is an alkyl group having 1 to 10 carbon atoms. Examples of such an alkyl group having 1 to 10 carbon atoms include methyl group, ethyl group, n-propyl group, iso-propyl group, n-butyl group, sec-butyl group, tert-butyl group, n-pentyl group, and hexyl group; and preferably, ethyl group.

In the formulas (2) and (5), X is H, Li, Na or K, and preferably Na.

Note that an optically active 2-(hydroxymethyl)-3-(3,4-methylenedioxyphenyl)-propionic ester derivative represented by the formula (4) and a 2-formylacetic ester derivative represented by the formula (5) are a novel compound not described in literature.

Next, a process for producing 2-formylacetic ester derivative represented by the formula (2) in the present invention will be described.

First, a derivative (1) having $R_1$ and $R_2$ defined above is industrially available or easily synthesized from industrially available materials. For example, ethyl 3-(3,4-methylenedioxypehnyl)-propionate can be easily prepared by hydrogenating 3,4-methylenedioxy cinnamic acid, followed by converting to ethyl ester.

A 2-formylacetic ester derivative represented by the formula (2) can be produced by reacting an acetic ester derivative represented by the formula (1) with a base and a formic ester in an appropriate solvent.

Examples of such a base include sodium hydride (NaH); lithium hydride (LiH); metallic sodium (Na); and alkaline metal alkoxides such as sodium methoxide (MeONa); sodium ethoxide (EtONa), sodium isopropoxide (iPrONa), and potassium tert-butoxide (tBuOK). Preferably, mention may be made of sodium hydride, metallic sodium, and an alkaline metal alkoxide, and more preferably sodium hydride (NaH).

The amount of a base to be used is preferably 1:1 to 1:15, more preferably 1:1 to 1:5, and still more preferably 1:1 to 1:3 in terms of the molar ratio of an acetic ester derivative (1) to a base (acetic ester derivative (1): a base).

Examples of the aforementioned formic ester include methyl formate, ethyl formate, n-propyl formate, iso-propyl formate, n-butyl formate, iso-butyl formate, and tert-butyl formate. Methyl formate and ethyl formate are preferable. Note that, in the reaction according to the present invention, alcohol is produced as a side product from a formic ester under basic conditions, so that an acetic ester derivative (1) is easily transesterificated by the side-product, alcohol. Then, the ester groups of the acetic ester derivative (1) and formic ester are desirably the same.

The amount of formic ester to be used is preferably 1:1 to 1:30, more preferably 1:1 to 1:10, and still more preferably 1:1 to 1:5 in terms of the molar ratio of an acetic ester derivative (1) to a formic ester (acetic ester derivative (1) a formic ester).

Examples of a solvent for use in this reaction include hydrocarbon-based solvents such as hexane, heptane, benzene, and toluene; ether-based solvents such as diethyl ether, tetrahydrofuran, 1,4-dioxane, tert-butylmethyl ether, and dimethoxyethane; halogen-based solvents such as methylene chloride, chloroform, and 1,1,1-trichloroethane; nitrogen-containing solvents such as dimethyl formamide, acetoamide, formamide, acetonitrile, and propionitrile; non-protic polar solvents such as dimethylsulfoxide, N-methylpyrrolidone, and hexamethylphosphoric triamide; and alcohol-based solvent such as methanol, ethanol, n-propanol, and n-butanol. The solvents may be used singly and in combination of two types or more.

The reaction temperature of the reaction is preferably −20 to 60° C., and more preferably, 0 to 50° C.

The reaction time of the reaction is preferably 1 to 72 hours, and more preferably, 1 to 20 hours.

In performing the reaction, a method of mixing individual reagents is not particularly limited. However, to perform the reaction in an industrial scale under safety control, a method of adding an acetic ester derivative and a formic ester simultaneously to a mixture of a base and a solvent is preferably employed. In this method, the acetic ester derivative added therein gradually starts a reaction. Thus, the reaction can be safely controlled by adjusting an addition speed of the derivative. The term "industrial scale" used herein refers to a reaction performed by subjecting a base in an amount of usually 1 kg or more, preferably 10 kg or more, more preferably 100 kg or more, and still more preferably 1000 kg or more, and most preferably 10000 kg or more.

The addition time of an acetic ester derivative and a formic ester varies depending upon the scale of the reaction, preferably 1 hour or more, more preferably 3 hours or more, and still more preferably, 5 hours or more. Furthermore, it is preferable that the addition time is 72 hours or less.

To perform the reaction more safely by this method, it is preferable to increase the concentration of a base. The concentration of the base in the mixture of the base and a solvent is not particularly defined, but usually not less than 10% by weight, preferably not less than 20% by weight, more preferably not less than 30% by weight, and most preferably not less than 40% by weight.

Furthermore, in the reaction method mentioned above, it is preferable that the substrate added in a mixture is allowed to react for a shorter time by increasing the reaction temperature, thereby controlling the reaction safely. The reaction temperature herein is not particularly defined, but usually 20° C. or more, preferably 30° C. or more, and more preferably 40° C. or more. The reaction temperature may be increased to a boiling point of the reaction solution.

When the reaction is performed in this method, it is particularly preferable that the concentration of the base is not less than 10% by weight and the reaction temperature is 20° C. or more.

Note that when the flowability of the reaction solution decreases with the progress of the reaction, a solvent may be added with the progress of the reaction in order to perform the reaction smoothly while maintaining appropriate stirring. More simply, it is sufficient that a solution containing an acetic ester derivative and a formic ester dissolved in a solvent, may be added.

After completion of the reaction, a 2-formyl acetic ester derivative represented by the formula (2) in the reaction solution is accompanied by a large amount of impurities deriving from various decomposition reactions and side reactions as well as the remaining raw materials, for example, the unreacted acetic ester derivative, formic ester, and the base-derived mineral oil. To obtain the target compound at a high purity, these impurities must be removed.

As a result of extensive studies by the present inventors, they have found that the 2-formylacetic ester derivative (2) and the reaction solution containing impurities are brought into contact with water, thereby successfully partitioning the alkaline metal salt of the 2-formylacetic ester derivative and impurities into the aqueous layer and the organic layer, respectively. After the obtained aqueous layer is acidified with an acid, the 2-formylacetic ester derivative (2) contained in the aqueous layer is extracted and concentrated with an organic solvent. In this manner, a process of simply removing the impurities into the organic layer and efficiently obtaining the target product with a high purity has been successively developed.

Now, an operation of isolating and purifying the 2-formylacetic ester derivative represented by the formula (2) will be described below. To remove impurities present with the 2-formylacetic ester derivative represented by the formula (2), water is added to the reaction solution containing the 2-formylacetic ester derivative (2) and impurities, thereby selectively transferring the alkaline metal salt of the 2-formylacetic ester derivative (2) into the aqueous layer. In this case, impurities such as the unreacted acetic ester derivative can be removed into the organic layer-containing the reaction solvent without virtually losing the target 2-formylacetic ester derivative (2).

Prior to addition of water, the reaction solution may be concentrated to reduce its volume. Alternatively, a common extraction solvent such as ethyl acetate, toluene, hexane, methylethyl ketone, tert-butylmethyl ether, diethyl ether, or methylene chloride may be added to the reaction solution in advance. After the alkaline metal salt of the 2-formylacetic ester derivative (2) is transferred and dissolved into the aqueous layer, the aqueous layer may be rewashed with the common extraction solvent, thereby further successfully reducing impurities.

Subsequently, the pH of the aqueous layer containing the 2-formylacetic ester derivative (2) with a high purity is adjusted to preferably 5 or less, and more preferably 3 or less by use of a common acid, for example, an inorganic acid such as hydrochloric acid or sulfuric acid, or an organic acid such as acetic acid or citric acid, and thereafter, the 2-formylacetic ester derivative (2) is extracted with the common extraction solvent mentioned above, followed by concentrating the solution. In this manner, the target product of a high chemical purity can be efficiently obtained.

The purity is preferably not less than 90% by weight, and more preferably, not less than 94% by weight.

On the other hand, in the case where extraction is performed by adding an acid to a reaction solution without a transferring operation where water is added to the reaction solution, both the target product, a 2-formylacetic ester derivative and impurities such as an unreacted acetic ester derivative are simultaneously extracted into an organic layer such as a reaction solvent. As a result, the target product cannot be obtained with a high purity.

Now, we will explain a process for producing an optically active 3-hydroxyproionic ester derivative represented by the formula (3) according to the present invention.

The optically active 3-hydroxyproionic ester derivative represented by the formula (3) can be obtained by stereoselectively reducing the formyl group of the formula (2) in the presence of an enzymatic source capable of stereoselectively reducing the formyl group of the 2-formylacetic ester derivative represented by the formula (2).

The term "enzymatic source" includes not only an enzyme per se having the aforementioned reducing activity and a cultured product of a microorganism having the reducing activity as well as a processed product thereof. The term "cultured product of a microorganism" refers to a culture solution containing microbial cells or cultured microbial cells. The term "a processed product thereof" refers to, for example, a crude extraction solution, lyophilized microorganism cell, microorganism cell dried with acetone, and ground cells of microorganism. These enzymatic sources can be used by immobilizing as an enzyme or microbial cell by a known means as they are. The immobilization can be performed by a known method to those skilled in the art (for example, crosslinking method, physical adsorption method and entrapment method).

In the enzymatic reduction step according to the present invention, such an enzymatic source capable of stereoselectively reducing the formyl group of a derivative represented by the formula (2) may be any one derived from a microorganism selected from the group consisting of the genera *Brettanomyces, Candida, Cryptococcus, Debaryomyces, Galactomyces, Ogataea, Pichia, Rhodotorula, Saccharomycopsis, Sporidiobolus, Sporobolomyces, Sterigmatomyces, Torulaspora, Trichosporon, Yamadazyma, Achromobacter, Cellulomonas, Devosia, Hafnia, Jensenia, Klebsiella, Proteus, Rhodococcus, Serratia, Cystofillobasidium, Williopsis, Yarrowia, Microbacterium*, and *Micrococcus*.

Of the enzymatic sources mentioned above, an enzymatic source capable of R-selectively reducing the formyl group of a derivative represented by the formula (2) includes preferably any one derived from a microorganism selected from the group consisting of the genera *Brettanomyces, Candida, Cryptococcus, Debaryomyces, Galactomyces, Ogataea, Pichia, Rhodotorula, Saccharomycopsis, Sporidiobolus, Sporobolomyces, Sterigmatomyces, Torulaspora, Trichosporon, Yamadazyma, Achromobacter, Cellulomonas, Devosia, Hafnia, Jensenia, Klebsiella, Micrococcus, Proteus, Rhodococcus*, and *Serratia*.

Of the enzymatic sources mentioned above, an enzymatic source capable of R-selectively reducing the formyl group of a derivative represented by the formula (2) includes preferably any one derived from a microorganism selected from the group consisting of

*Brettanomyces anomalus, Candida cantarellii, Candida glaebosa, Candida gropengiesseri, Candida lactis-condensi, Candida magnoriae, Candida maltosa, Candida maris, Candida mogii, Candida pini, Candida rugosa, Candida sorbophila, Candida tropicalis, Candida versatilis, Cryptococcus curvatus, Cryptococcus terreus, Debaryomyces nepalensis, Debaryomyces robertsiae, Galactomyces reessii, Ogataea minuta* var. *minuta, Pichia canadensis, Pichia silvicola, Pichia xylosa, Rhodotorula aurantiaca, Rhodotorula glutinis, Rhodotorula graminis, Rhodotorula lactosa, Saccharomycopsis selenospora, Sporidiobolus johnsonii, Sporidiobolus salmonicolor, Sporobolomyces salmonicolor, Sterigmatomyces halophilus, Torulaspora delbrueckii, Trichosporon asteroides, Yamadazyma stipitis, Achromobacter xylosoxidans* subsp. *denitrificans, Cellulomonas fimi, Cellulomonas* sp., *Cellulomonas uda, Devosia riboflavina, Hafnia alvei, Jensenia canicruria, Klebsiella planticola, Micrococcus luteus, Proteus inconstans, Rhodococcus erythropolis, Rhodococcus equi, Rhodococcus* sp., and *Serratia marcescens*.

An enzymatic source capable of S-selectively reducing the formyl group of a derivative represented by the formula (2) includes preferably any one derived from a microorganism selected from the group consisting of the genera *Candida, Cystofillobasidium, Pichia, Rhodotorula, Torulaspora, Williopsis, Yarrowia, Devosia, Microbacterium* and *Micrococcus*.

An enzymatic source capable of S-selectively reducing the formyl group of a derivative represented by the formula (2) includes preferably any one derived from a microorganism selected from the group consisting of *Candida magnoliae, Cystofillobasidium bisporidii, Pichia bispola, Rhodotorula glutinis* var. *glutinis, Torulaspora globosa, Williopsis saturnus* var. *mrakii, Williopsis saturnus* var. *saturnus, Yarrowia lipolytica, Devosia riboflavina, Microbacterium esteraromaticum*, and *Micrococcus luteus*.

As a microorganism capable of producing a reduction enzyme derived from the microorganism, either a wild type or a mutant type may be used. Alternatively, a microorganism transformed by a genetic engineering such as cell fusion and gene manipulation may be used. The genetically manipulated microorganism producing such an enzyme can be obtained by a process comprising a step of isolating and/or purifying the enzyme to determine a part or whole of the amino acid sequence of the enzyme, a step of obtaining a DNA sequence encoding the enzyme based on the amino acid sequence, a step of obtaining a recombinant microorganism by introducing the DNA into another microorganism, and a step of culturing the recombinant microorganism to obtain the enzyme (the pamphlet of WO98/35025).

Any culture medium may be used for culturing a microorganism to be used as an enzymatic source as long as the microorganism can proliferate therein. For example, a general liquid medium containing the following nutritional sources may be used. Examples of a carbon source include saccharides such as glucose and sucrose, alcohols such as ethanol and glycerol; fatty acids such as oleic acid and stearic acid and esters thereof; and oils such as rapeseed oil and soybean oil.

Examples of a nitrogen source include ammonium sulfate, sodium nitrate, diammonium hydrogenphosphate, peptone, casamino acid, corn steep liquor, bran, and a yeast extract.

Examples of an inorganic salt include sulfates such as magnesium sulfate, zinc sulfate, iron sulfate, copper sulfate, and manganese sulfate; sodium chloride, calcium carbonate, dipotassium hydrogenphosphate, and potassium dihydrogenphosphate.

Examples of other nutrition sources may include a malt extract and meat extract.

Culturing is performed aerobically, usually for about 1 to 5 days in a medium at pH 3 to 9 and at a culturing temperature of 10 to 50° C.

The reduction reaction of the present invention can be performed by adding a substrate, the 2-formylacetic ester derivative (2), a coenzyme NAD(P)H, and a cultured product of the microorganism or a processed product thereof to an appropriate solvent and stirring while controlling pH.

As a solvent to be used the reduction reaction, ethyl acetate, butyl acetate, toluene, and hexane may be added.

Reaction conditions vary depending upon the enzyme, microorganism or processed product thereof, substrate concentration to be employed. A substrate is usually used in a concentration of about 0.1 to 100% by weight, and preferably 1 to 60% by weight.

The concentration of coenzyme NAD(P)H is usually 0.0001 to 100% by mole, and preferably, 0.0001 to 0.1% by mole based on the substrate.

The reaction temperature is usually 10 to 60° C. and preferably 20 to 50° C.

The pH of the reaction is usually 4 to 9 and preferably 5 to 8.

The time of the reaction is usually 1 to 120 hours and preferably 1 to 72 hours.

The reaction can be performed by adding a substrate at a time or continuously. The reaction may be performed in a batch or continuous process.

In the reduction step of the present invention, the amount of an expensive coenzyme in use can be significantly reduced by using a coenzyme NAD (P) H regeneration system generally used in combination. Examples of a representative NAD(P)H regeneration system include a method using glucose dehydrogenase and glucose.

When the same reduction reaction as above is performed using a cultured product of a microorganism, which has beeb transformed by introducing a gene of a reduction enzyme and a gene of an enzyme (e.g., glucose dehydrogenase) capable of regenerating a coenzyme upon which the reduction enzyme is dependent, into a same host microorganism, or a processed product of the microorganism, an optically active 3-hydroxypropionic ester derivative can be produced at a lower cost since an enzymatic source required for the regeneration of coenzyme needs not separately prepared.

Examples of such a transformed microorganism as mentioned above include one transformed with a plasmid having DNA encoding the reduction enzyme and DNA encoding an enzyme capable of regenerating a coenzyme upon which the reduction enzyme is dependent. As such an enzyme capable of regenerating an enzyme, glucose dehydrogenase is preferable and glucose dehydrogenase derived from *Bacillus megaterium* is more preferable. Furthermore, as a host microorganism, *Escherichia coli* is preferable.

More preferably, examples of such a transformed microorganism include:

*Escherichia coli* HB101 (pNTCRG) (Accession Number: FERM BP-6898, deposited on Sep. 28, 1999) transformed with a reduction enzyme gene derived from *Candida magnoliae* IFO0705 and a glucose dehydrogenase gene derived from *Bacillus megaterium*;

*Eseherichia coli* HB101 (pNTDRG1) (Accession Number: FERM BP-08458, deposited on Aug. 25, 2003) transformed with a reduction enzyme gene derived from *Devosia riboflavina* IFO13584 and a glucose dehydrogenase gene derived from *Bacillus megaterium*;

*Escherichia coli* HB101 (pNTRGG1) (Accession Number: FERM BP-7858, deposited on Jan. 22, 2002) transformed with a reduction enzyme gene derived from *Rhodotorula glutinis* IFO0415 and a glucose dehydrogenase gene derived from *Bacillus megaterium*;

*Eseherichia coli* HB101 (pNTSGG1) (Accession Number: FERM P-48449, deposited on Aug. 6, 2001), transformed with a reduction enzyme gene derived from *Serratia marcescens*IFO12468 and a glucose dehydrogenase gene derived from *Bacillus megaterium*;

*Escherichia coli* HB101 (pTSBG1) (Accession Number: FERM BP-7119, deposited on Apr. 11, 2000), transformed with a reduction enzyme gene derived from *Micrococcus luteus IFO*13867 and a glucose dehydrogenase gene derived from *Bacillus megaterium*; and

*Escherichia coli* HB101 (pNTRS) (Accession Number: FERM BP-08545, deposited on Nov. 10, 2003), transformed with a reduction enzyme gene.

These transformed microorganisms have been deposited at the International Patent Organism Depositary of the National Institute of Advanced Industrial Science Technology (located at Tsukuba Central 6, 1-1-1 Higashi, Tsukuba, Ibaraki, Japan). Of them, *Escherichia coli* HB101 (pNTCRG), *Escherichia coli* HB101 (pNTDRG1), *Escherichia coli* HB101 (pNTRGG1), *Escherichia coli* HB101 (pTSBG1), and *Escherichia coli* HB101 (pNTRS) have been internationally deposited under the Budapest Treaty.

In case that the reduction step of the present invention is performed in combination with a coenzyme regeneration system or by using a cultured product of a transformed microorganism as mentioned above or a processed product thereof as an enzyme source, such a reaction may be performed by adding an oxidative type NAD (P) lower in cost as a coenzyme.

An optically active 3-hydroxypropionic ester derivative (3) produced through the reduction reaction can be purified by any customary method. For example, when a microorganism is used as an enzymatic source, optically active ethyl 2-(hydroxymethyl)-3-phenylpropionate can be purified by removing suspended matters such as microbial cells, if necessary, by centrifugation and filtration, extracting the product with an organic solvent such as ethyl acetate or toluene, removing the organic solvent under reduced pressure and distilling the product under reduced pressure or treating it chromatographically.

Best Mode for Carrying Out the Invention

The present invention will be described more specifically by way of examples, which should not be construed as limiting the invention.

REFERENCE EXAMPLE 1

Preparation of 3-(3,4-methylenedioxyphenyl)-propionic ethyl ester

First, 50 g of 3,4-methylenedioxy cinnamic acid was dissolved in 500 ml of ethanol. To the mixture, 5 g of 5% Pd/C catalyst was added. The reaction system was replaced with hydrogen gas and stirred at 25° C. for 6 hours. After completion of the reaction, the Pd/C catalyst was removed by filtration. The resultant ethanol solution was cooled to 5° C. and 37.1 g of thionyl chloride was added dropwise for one hour. After completion of the dropwise addition, the ethanol solution was stirred for a further 3 hours with keeping the inner temperature at 5° C. After completion of the reaction, a solvent was distilled off under reduced pressure to obtain 54.7 g of an orange concentrate. A part of the concentrate was taken and analyzed by high performance column chromatography (HPLC) (column: LiChrosphere 100 PR-8(E), 250 mm×4.0 mm I.D., manufactured by Merck Ltd., mobile phase: an aqueous solution of phosphate/potassium dihydrogenphosphate: acetonitrile=1:1, flow rate: 1 ml/minute, detection wavelength: 210 nm, column temperature: 30° C.). As a result, it was observed that 49.8 g of the titled compound was obtained.

$^1$H NMR (400 Hz, CDCl$_3$) δ: 6.77-6.63 (3H, m), 5.93 (2H, s), 4.17-4.10 (2H, q), 2.86 (2H, t), 2.56 (2H, t), 1.27 (3H, t).

REFERENCE EXAMPLE 2

Process for Producing ethyl 2-formyl-3-phenylpropionate

To a suspension solution containing 4.4 g of 60% NaH in 200 ml of THF, 17.8 g of ethyl 3-phenylpropionate and 8.2 g of ethyl formate were added dropwise under ice cool for one hour. Thereafter, the mixture was stirred at room temperature for 15 hours. Furthermore, 14 g of 60 % NaH and 25.9 g of ethyl formate were divided into three parts and each part was added separately. Afterwards, the solution mixture was stirred at room temperature for 15 hours. After a 10% citric acid solution was added to the resultant reaction solution, the reaction solution was extracted with ethyl acetate and the extract was concentrated under reduced pressure to obtain 32.4 g of a brown oily concentrate. The concentrate thus obtained was purified by silica gel column chromatography to obtain 17.9 g of the titled compound as a transparent oily substance.

REFERENCE EXAMPLE 3

Process for Producing methyl 2-formyl-3-phenylpropionate

The titled compound was obtained as a transparent oily substance in accordance with the same manner as in Reference Example 2 except that methyl 3-phenylpropionate and methyl formate were used in place of ethyl 3-phenylpropionate and ethyl formate.

REFERENCE EXAMPLE 4

Process for Producing isopropyl 2-formyl-3-phenylpropionate

The titled compound was obtained as a transparent oily substance in accordance with the same manner as in Reference Example 2 except that isopropyl 3-phenylpropionate and isopropyl formate were used in place of ethyl 3-phenylpropionate and ethyl formate.

REFERENCE EXAMPLE 5

Process for Producing isobutyl 2-formyl-3-phenylpropionate

The titled compound was obtained as a transparent oily substance in accordance with the same manner as in Reference Example 2 except that isobutyl 3-phenylpropionate and isobutyl formate were used in place of ethyl 3-phenylpropionate and ethyl formate.

EXAMPLE 1

Process for Producing ethyl 2-formyl-3-(3,4-methylenedioxyphenyl)-propionate

First, 42.4 g of 60% NaH was suspended in 500 ml of tetrahydrofuran (THF). 84.5 g (purity: 93.7% by weight) of ethyl 3-(3,4-methylenedioxyphenyl)-propionate was dissolved in 100 ml of THF and added dropwise to the suspension solution prepared above at room temperature. After the resultant suspension solution was raised in temperature to 40° C. and stirred for 15 minutes, 131 g of ethyl formate was added dropwise for 2.5 hours to the suspension solution and stirred for a further 3 hours.

The reaction solution was concentrated to about a half amount by evaporating the solvent and cooled in an ice bath. Thereafter, 500 ml of water was added dropwise at such a rate that allowed to maintain the inner temperature at 10° C. or less. The aqueous layer was washed twice with 200 ml of hexane and the pH of the solution was adjusted to 4.5 with concentrated hydrochloric acid. The solution was extracted three times with 500 ml of toluene and then subjected to concentration under reduced pressure to obtain 82.8 g of the titled compound. The chemical purity of the compound was analyzed by gas chromatography (GC) in the following conditions, and was found to be 94.7% by weight.

GC Analysis Conditions:
Column: TC-FFAP 1 m×0.25 mm I.D. (manufactured by GL Science Inc.), Carrier gas: He=8 kpa, detection: FID, Column temperature: 150° C., Detection time: 4.0 minutes in the case of ethyl 2-formyl-3-(3,4-methylenedioxyphenyl)-propionate.

EXAMPLE 2

Process for Producing ethyl 2-formyl-3-(3,4-methylenedioxyphenyl)-propionate

First, 7.91 g of 60% NaH was suspended in 12 ml of THF and the solution was raised in temperature to 40° C. 11.0 g of ethyl 3-(3,4-methylenedioxyphenyl)-propionate and 11.0 g of ethyl formate were dissolved in 77.0 ml of THF and added dropwise to the suspension solution prepared above for 5 to 14 hours. After the suspension solution was stirred for one hour, 3.7 g of ethyl formate was added dropwise to the suspension solution for 5 hours and stirred for a further 12 hours.

To the obtained reaction mixture, 250 ml of toluene was added and the reaction mixture was concentrated under reduced pressure to obtain an about 10% by weight toluene suspension solution. The suspension solution was added dropwise to 55 ml of water cooled at 10° C. or less at such a rate that allowed to maintain the inner temperature. After the organic layer was discarded, the aqueous layer was washed once with 180 ml of toluene, adjusted to pH 5 to 7 with concentrated hydrochloric acid, and extracted twice with 90 ml of toluene. After washed once with water, the organic layer was concentrated under reduced pressure to obtain 11.2 g of the titled compound. The chemical purity of the compound, as analyzed in accordance with the process of Example 1, was 98.8% by weight.

EXAMPLE 3

Process for Producing methyl 2-formyl-3-(3,4-methylenedioxyphenyl)-propionate

First, 1.38 g of 60% NaH was suspended in 12 ml of THF. Then, 2.4 g of methyl 3-(3,4-methylenedioxyphenyl)-propionate was dissolved in 12 ml of THF and added dropwise to the suspension solution prepared above at room temperature. After the suspension solution was raised in temperature to 40° C. and stirred for 15 minutes, 3.46 g of methyl formate was added dropwise for 1 hour. Further, 0.7 g of 60% NaH and 0.9 g of methyl formate were divided into four parts and each part was added separately. Afterwards, the solution mixture was stirred at 40° C. for 3 hours.

After a solvent was distilled off and the reaction solution was concentrated to about a half amount, the reaction solution was cooled in an ice bath and 40 ml of water was added dropwise at a rate that allowed to maintain the inner temperature at 10° C. or less. The aqueous layer was washed twice with 50 ml of toluene and adjusted with concentrated hydrochloric acid to pH 4.5. This was extracted twice with 50 ml of toluene and the extract was concentrated under reduced pressure to obtain 2.63 g of the titled compound. The chemical purity, as analyzed in accordance with the process of Example 1, was 96.4% by weight.

EXAMPLE 4

Process of Producing ethyl 2-formylhexanoate

First, 60 g of 60% NaH was suspended in 600 ml of THF and 72.1 g of ethyl hexanoate was added dropwise to the suspension solution thus prepared at room temperature. After the suspension solution was raised in temperature to 40° C. and stirred for 15 minutes, 185.2 g of ethyl formate was added dropwise for 6 hours. Furthermore, 30 g of 60% NaH and 92.6 g of ethyl formate were divided into four parts and each part was added separately. Afterward, the solution mixture was stirred at 40° C. for 3 hours.

After the solvent was distilled off and the reaction solution was concentrated to about a half amount, the reaction solution was cooled in an ice bath and 40 ml of water was added dropwise at a rate that allowed to maintain the inner temperature at 10° C. or less. The aqueous layer was washed twice with 400 ml of toluene and adjusted to pH 4.5 with concentrated hydrochloric acid. This was extracted twice with 700 ml of toluene and the extract was concentrated under reduced pressure to obtain 76.8 g of the titled compound. The chemical purity, as analyzed in accordance with the following method, was 96.6% by weight.

GC Analysis Conditions:

Column: HP-5, 30 m×0.32 mm I.D. (manufactured by J&W Scientific Inc.), Carrier gas: He=125 kPa, Detection: FID, Column temperature: 120° C., Detection time: 6.9 minutes for ethyl 2-formylhexanoate, and 9.8 minutes for ethyl 2-hydroxymethylhexanoate.

$^1$H NMR (400 Hz, CDCl$_3$) δ: 11.42 (0.6H, d), 9.70 (0.4H, d), 7.0 (0.6H, d), 4.16-4.27 (2H, m), 3.25 (0.4H, m), 1.24-2.37 (9H, m), 0.90 (3H, t).

EXAMPLE 5

Process for Producing ethyl 2-formylhexanoate

First, 62 g of 60% NaH was suspended in 126 ml of THF and the suspension was raised in temperature to 40° C. 56 g of ethyl hexanoate and 86 g of ethyl formate were dissolved in 250 ml of THF and added dropwise to the suspension solution prepared above for 5 to 20 hours. After stirring for three hours, 86 g of ethyl formate was added for 5 hours and the solution mixture was stirred for a further 12 hours.

To the resultant reaction mixture, 1,200 ml of toluene was added and the resultant mixture was concentrated under reduced pressure to obtain an about 10% by weight toluene suspension solution. This was added dropwise to 280 ml of water cooled to 10° C. or less at a rate that allowed to maintain the inner temperature. After the organic layer was discarded, the aqueous layer was washed once with 570 ml of toluene. The aqueous layer was adjusted to pH 5 to 7 with concentrated hydrochloric acid, and then extracted twice with 280 ml of ethyl acetate. After washed once with water, the organic layer was concentrated under reduced pressure to obtain 55 g of the titled compound. The chemical purity, as analyzed in accordance with the process of Example 4, was 97.2% by weight.

EXAMPLE 6

Process for Producing ethyl 2-formylbutyrate

The titled compound was obtained as a brown oily substance in accordance with the process of Example 4 except that ethyl butyrate was used in place of ethyl hexanoate. The chemical purity, as analyzed in accordance with the process of Example 4, was 96.4% by weight.

$^1$H NMR (400 Hz, CDCl$_3$) δ: 11.42 (0.6H, d), 9.70 (0.4H, d), 7.0 (0.6H, d), 4.15-4.28 (2H, m), 3.17-3.21 (0.4H, m), 1.23-2.29 (5H, m), 0.96-1.05 (3H, m).

EXAMPLE 7

Process for Producing ethyl 2-formylheptanoate

The titled compound was obtained as a brown oily substance in accordance with the process of Example 4 except that ethyl heptanoate was used in place of ethyl hexanoate. The chemical purity, as analyzed in accordance with the process of Example 4, was 96.7% by weight.

$^1$H NMR (400 Hz, CDCl$_3$) δ: 11.43 (0.6H, d), 9.70 (0.4H, d), 7.1 (0.6H, d), 4.16-4.27 (2H, m), 3.23-3.27 (0.4H, m), 1.21-2.06 (11H, m), 0.85-0.91 (3H, m).

EXAMPLE 8

Process for Producing ethyl 2-formyloctanoate

The titled compound was obtained as a brown oily substance in accordance with the process of Example 4 except that ethyl octanoate was used in place of ethyl hexanoate. The chemical purity, as analyzed in accordance with the process of Example 4, was 95.4% by weight.

$^1$H NMR (400 Hz, CDCl$_3$) δ: 11.43 (0.6H, d), 9.70 (0.4H, d), 7.0 (0.6H, d), 4.16-4.27 (2H, m), 3.23-3.27 (0.4H, m), 1.25-1.88 (13H, m), 0.88 (3H, t).

COMPARATIVE EXAMPLE 1

Process for Producing ethyl 2-formyl-3-(3,4-methylenedioxyphenyl)-propionate First 2.0 g of 606 NaH was suspended in 30 ml of THF and the suspension solution was cooled to 0° C. Then, 6.0 g of ethyl 3-(3,4-methylenedioxyphenyl)-propionate (purity: 92.1% by weight) was dissolved in 20 ml of THF and added dropwise to the suspension solution prepared above. After 4 ml of ethyl formate was added at 0° C., the solution was returned to room temperature and stirred for a further 20 minutes. The reaction solution was heated to 40° C. and stirring was further continued. About 30 minutes after heating, gas generation was observed. After completion of gas generation, the reaction solution was analyzed by HPLC (Column: LiChrosphere 100 PR-8(E), 250 mm×4.0 mm I.D., manufactured by Merck Ltd., Mobile phase: an aqueous solution of phosphate/potassium dihydrogenphosphate: acetonitrile=1:1, flow rate: 1 ml/minute, detection wavelength: 210 nm, column temperature: 30° C.), it was observed that raw materials remained. Then, 1 g of NaH and 4 ml of ethyl formate were added to the reaction solution and stirred at 40° C. Gas generation started again and completed in about 15 minutes. As the reaction solution was analyzed again, the raw materials were observed to still remain. Then, 1 g of NaH and 4 ml of ethyl formate were added to the reaction solution. After completion of gas generation, the reaction solution was analyzed again. Since the raw materials were observed to slightly remain, further 1 g of NaH and 8 ml of ethyl formate were added to the reaction solution. Since the raw materials were observed to completely disappear, the reaction was terminated. After pH was adjusted to 7 to 8 with hydrochloric acid, ethyl acetate was added to perform extraction. Mineral oil contained in NaH was removed by a separatory funnel in accordance with a liquid-separatory operation. The obtained ethyl acetate layer was concentrated to obtain 4.75 g of the titled compound as an orange oil. The chemical purity, as analyzed in accordance with the process of Example 1, was 80.20% by weight.

EXAMPLE 9

Process for Producing Optically Active ethyl 2-(hydroxymethyl)-3-phenylpropionate A liquid medium (pH 7.0) was prepared so as to contain 4% of glucose, 0.3% of yeast extract, 1.3% of KH$_2$PO$_4$, 0.7% of (NH$_4$)$_2$HPO$_4$, 0.01% of NaCl, 0.08% of MgSO$_4$.7H$_2$O, 0.006% of ZnSO$_4$.7H$_2$O, 0.009% of FeSO$_4$.7H$_2$O, 0.0005% of CuSO$_4$.5H$_2$O, and 0.001% of MnSO$_4$.4 to 5 H$_2$O. The liquid medium was dispensed to large test tubes in an amount of 5 ml per each tube and the test tubes were sterilized by steam at 120° C. for 20 minutes. The liquid medium was inoculated with each of the microorganisms shown in Table 1 by a platinum loop and the medium was incubated with shaking at 30° C. for 2 to 3 days. Microbial cells were centrifugally collected from the culture solution, washed with water and suspended in 1 ml of a 0.1 M phosphate buffer (pH 6.5). 0.5 ml of the microbial cell suspension solution, 2 mg of ethyl 2-formyl-3-phenylpropionate, and 0.5 ml of a 0.1 M phosphate buffer containing 20 mg of glucose were mixed, placed in each test tube with a cap, and shaken at 30° C. for 24 hours. After the reaction, the reaction solution was extracted with ethyl acetate of the same volume. The amounts of the substrate and the product in the extract were analyzed by gas chromatographic (GC) method to obtain a conversion rate (%). The product was purified by thin-layer chromatography (TLC) and analyzed by HPLC to determine its optical purity. The results are shown in Table 1 (conversion rates are 20 to 100%).

The analysis conditions and calculation methods for the conversion rate and the optical purity are as follows.

GC Analysis Conditions:
Column: TC-FFAP, 5 m×0.25 mm I.D. (manufactured by GL Science Inc.), Carrier gas: He=30 kPa, Detection: FID, Column temperature: 150° C., Detection time: 4.0 minutes in the case of ethyl 2-formyl-3-phenylpropionate: 12.0 minutes in the case of ethyl 2-hydroxymethyl-3-phenylpropionate.

HPLC Analysis Conditions:
Column: Chiralcel AS, 250 mm×4.6 mm I.D. (manufactured by Daicel Chemical Industries, Ltd.), Eluant: hexane: isopropanol=98:2, Flow rate: 1.0 ml/min. Detection: 210 nm, Column temperature: 40° C., Detection time: 16.1 minutes for R configuration and 18.3 minutes for S configuration.

Conversion rate (%)=Product amount/(substrate amount+product amount)×100

Optical purity (% $ee$)=$(A-B)/(A+B)$×100 (A and B represent the amounts of corresponding enantiomers and A>B).

TABLE 1

| Microorganism | | Optical purity % e.e. | Steric configuration |
|---|---|---|---|
| Brettanomyces anomalus | IFO 0627 | 86.8 | (R) |
| Candida cantarellii | IFO 1261 | 53.1 | (R) |
| Candida glaebosa | IFO 1353 | 6.0 | (R) |
| Candida gropengiesseri | IFO 0659 | 77.8 | (R) |
| Candida lactis-condensi | IFO 1286 | 87.1 | (R) |
| Candida magnoliae | IFO 0705 | 65.5 | (R) |
| Candida maltosa | IFO 1977 | 70.3 | (R) |
| Candida maris | IFO 10003 | 75.2 | (R) |
| Candida mogii | IFO 0436 | 43.8 | (R) |
| Candida pini | IFO 1327 | 53.1 | (R) |
| Candida rugosa | IFO 0591 | 64.6 | (R) |
| Candida sorbophila | IFO 1583 | 90.1 | (R) |
| Candida tropicalis | IFO 1403 | 78.5 | (R) |
| Candida versatilis | IFO 1228 | 88.1 | (R) |
| Cryptococcus curvatus | IFO 1159 | 17.6 | (R) |
| Cryptococcus terreus | IFO 0727 | 37.3 | (R) |
| Debaryomyces nepalensis | IFO 0039 | 72.0 | (R) |
| Debaryomyces robertsiae | IFO 1277 | 60.8 | (R) |
| Galactomyces reessii | IFO 10823 | 72.2 | (R) |
| Ogataea minuta var. minuta | IFO 0975 | 78.1 | (R) |
| Pichia canadensis | IFO 0976 | 68.7 | (R) |
| Pichia canadensis | IFO 0973 | 77.4 | (R) |
| Pichia silvicola | IFO 0807 | 37.4 | (R) |
| Pichia xylosa | IFO 0950 | 43.9 | (R) |
| Rhodotorula aurantiaca | IFO 0754 | 4.5 | (R) |
| Rhodotorula graminis | IFO 0190 | 32.5 | (R) |
| Rhodotorula lactosa | IFO 1423 | 16.5 | (R) |

TABLE 1-continued

| Microorganism | | Optical purity % e.e. | Steric configuration |
|---|---|---|---|
| Saccharomycopsis selenospora | IFO 1850 | 54.8 | (R) |
| Sporidiobolus johnsonii | IFO 6903 | 40.0 | (R) |
| Sporidiobolus salmonicolor | IFO 1035 | 6.0 | (R) |
| Sporobolomyces salmonicolor | IFO 1038 | 4.8 | (R) |
| Sterigmatomyces halophilus | IFO 1488 | 23.6 | (R) |
| Torulaspora delbrueckii | IFO 0381 | 90.6 | (R) |
| Trichosporon asteroides | IFO 0173 | 47.7 | (R) |
| Yamadazyma stipitis | IFO 10063 | 17.0 | (R) |
| Cystqfillobasidium bisporidii | IFO 1927 | 24.8 | (S) |
| Pichia bispola | IFO 0803 | 13.3 | (S) |
| Rhodotorula glutinis var. glutinis | IFO 0697 | 43.7 | (S) |
| Torulaspora globosa | IFO 0016 | 76.5 | (S) |
| Williopsis saturnus var. mrakii | IFO 0895 | 9.3 | (S) |
| Williopsis saturnus var. saturnus | IFO 0992 | 10.8 | (S) |
| Yarrowia lipolytica | IFO 0746 | 4.4 | (S) |

EXAMPLE 10

Process for Producing Optically Active ethyl 2-(hydroxymethyl)-3-phenylpropionate Conversion rate and optical purity were determined in accordance with the same manner as in Example 9 except that each of the microorganisms shown in Table 2 was cultured in a liquid medium (pH 7.0) consisting of 1.5% of glycerin, 0.5% of yeast extract, 1.3% of $KH_2PO_4$, 0.7% of $(NH_4)_2HPO_4$, 0.01% of NaCl, 0.08% of $MgSO_4.7H_2O$, 0.006% of $ZnSO_4.7H_2O$, 0.009% of $FeSO_4.7H_2O$, 0.0005% of $CuSO_4.5H_2O$, and 0.001% of $MnSO_4.4$ to $5 H_2O$. The results are shown in Table 2 (conversion rates are 20 to 100%).

TABLE 2

| Microorganism | | Optical purity % e.e. | Steric configuration |
|---|---|---|---|
| Achromobacter xylosoxidans subsp. denitrificans | IFO 15125 | 83.4 | (R) |
| Cellulomonas fimi | IFO 15513 | 63.6 | (R) |
| Cellulomonas sp. | JCM 2471 | 65.4 | (R) |
| Cellulomonas uda | IFO 3747 | 19.3 | (R) |
| Hafnia alvei | IFO 3731 | 85.6 | (R) |
| Jensenia canicruria | IFO 13914 | 74.2 | (R) |
| Klebsiella planticola | IFO 3317 | 80.1 | (R) |
| Proteus inconstans | IFO 12931 | 81.6 | (R) |
| Rhodococcus erythropolis | IFO 12320 | 75.8 | (R) |
| Rhodococcus equi | IFO 3730 | 88.5 | (R) |
| Microbacterium esteraromaticum | IFO 3752 | 25.5 | (S) |

EXAMPLE 11

Process for Producing Optically Active ethyl 2-(hydroxymethyl)-3-phenylpropionate A liquid medium (pH 7.0) was prepared so as to contain 4% glucose, 0.3% of yeast extract, 1.3% of $KH_2PO_4$, 0.7% of $(NH_4)_2HPO_4$, 0.01% of NaCl, 0.08% of $MgSO_4.7H_2O$, 0.006% of $ZnSO_4.7H_2O$, 0.009% of $FeSO_4.7H_2O$, 0.0005% of $CuSO_4.5H_2O$, and 0.001% of $MnSO_4.4$ to $5 H_2O$. The liquid medium was dispensed to large test tubes in an amount of 5 ml per each tube and the test tubes were sterilized by steam at 120° C. for 20 minutes. The liquid medium was inoculated each of the microorganisms shown in Table 3 by a platinum loop and incubated with shaking at 30° C. for 2 to 3 days. Microbial cells were centrifugally collected from each culture solution, and washed with water. After ice cold acetone was added, the cells were dried under reduced pressure to obtain acetone dried microbial cells. 5 mg of the acetone dried microbial cells, 2 mg of ethyl 2-formyl-3-phenylpropionate, 10 mg of glucose, 1 mg of NAD (or NADP), 0.5 ml of 0.1M phosphate buffer (pH=6.5) and 0.5 ml of ethyl acetate were added to each test tube with a cap and shaken at 30° C. for 24 ours. Subsequently, the same operation as in Example 9 was performed to determine a conversion rate and optical purity. The results are shown in Table 3.

TABLE 3

| Microorganism | | NAD | | NADP | |
|---|---|---|---|---|---|
| | | Conversion rate % | Optical purity % e.e. | Conversion rate % | Optical purity % e.e. |
| Candida magnoliae | IFO 0705 | <2 | — | 10.0 | 35.3 |
| Candida maris | IFO 10003 | <2 | — | 4.1 | 97.4 |
| Candida sorbophila | IFO 1583 | <2 | — | 44.2 | 31.8 |
| Candida tropicalis | IFO 1403 | <2 | — | 18.0 | 38.5 |
| Candida versatilis | IFO 1228 | <2 | — | 3.2 | 23.5 |
| Ogataea minuta var. minuta | IFO 0975 | <2 | — | 52.6 | 99.1 |
| Pichia canadensis | IFO 0976 | <2 | — | 53.6 | 98.0 |
| Pichia canadensis | IFO 0973 | <2 | — | 72.3 | 96.4 |
| Pichia silvicola | IFO 0807 | <2 | — | 11.6 | 83.1 |
| Saccharomycopsis selenospora | IFO 1850 | <2 | — | 9.7 | 33.6 |
| Torulaspora globosa | IFO 0016 | 55.1 | 82.5 | 49.6 | 53.8 |

EXAMPLE 12

Process for Producing Optically Active ethyl 2-hydroxymethylalkanoate

First, 5 mg of the acetone dried microbial cells obtained in Example 11, 2 mg of each type of the ethyl 2-formylalkanoates shown in Table 4, 10 mg of glucose, 1 mg of NADP, 0.5 ml of 0.1M phosphate buffer (pH=6.5), and 0.5 ml of ethyl acetate were added to each test tube with a cap and shaken at 30° C. for 24 hours. After the reaction, the reaction solution was extracted with ethyl acetate of the same volume. The amounts of the substrate and the product in the extract were analyzed by gas chromatographic (GC) method to obtain the conversion rate (%). The product was derivatized with a HPLC labeling agent (3,5-dinitrobenzoyl chloride), and purified by thin-layer chromatography (TLC), and thereafter analyzed by HPLC to determine the optical purity. The results are shown in Table 4. The analysis conditions are shown below.

GC Analysis Conditions:
Column: HP-5, 30 m×0.32 mm I.D. (manufactured by J&W Scientific Inc.), Carrier gas: He=125 kPa, Detection: FID, Column temperature: 120° C., Detection time: 6.9 minutes for ethyl 2-formylhexanoate and 9.8 minutes for ethyl 2-hydroxymethylhexanoate;

HPLC Analysis Condition:
Column: Chiralcel OD-H, 0.46×25 cm I.D. (manufactured by Daicel Chemical Industries, Ltd.), Eluant: hexane:isopropanol=95:5, Flow rate: 0.5 ml/min. Detection: 2.10 nm, Column temperature: 40° C., Detection time: 3.06 minutes for a (R)-2-hydroxymethylhexanoic ethyl derivative and 37.4 minutes for a (S)-2-hydroxymethyl hexanoic ethyl derivative.

TABLE 4

| Microorganism | Substrate | Conversion rate % | Optical purity % e.e. |
|---|---|---|---|
| Ogataea minuta var. minuta IFO 0975 | Ethyl 2-formylbutyrate | 90 | 88.7 |
| | Ethyl 2-formylhexanoate | 45 | 96.7 |
| | Ethyl 2-formyloctanoate | 41 | 75.0 |
| Pichia Canadensis IFO 0976 | Ethyl 2-formylbutyrate | 63 | 37.5 |
| | Ethyl 2-formylhexanoate | 35 | 74.6 |
| | Ethyl 2-formyloctanoate | 63 | 87.0 |
| Pichia Canadensis IFO 0973 | Ethyl 2-formylbutyrate | 89 | 48.1 |
| | Ethyl 2-formylhexanoate | 55 | 91.5 |
| | Ethyl 2-formyloctanoate | 61 | 71.0 |

EXAMPLE 13

Process for Producing Optically Active 2-(hydroxymethyl)-3-phenylpropionic ester Recombinant *Escherichia coli* HB101 (PNTCRG) (Accession Number: FERM BP-6898) was inoculated in 50 ml of 2×YT medium (containing 1.6% of tripeptone, 1.0% of yeast extract, and 0.5% of NaCl, pH=7.0) sterilized in a 500-ml Sakaguchi Flask and incubated while shaking at 37° C. for 18 hours. To 1 ml of the resultant culture solution, 10 mg of each type of the 2-formyl-3-phenylpropionic esters shown in Table 5, 1 mg of NADP, and 10 mg of glucose were added and the mixture was stirred at 30° C. for 2 hours. After completion of the reaction, the conversion rate and optical purity of the product were analyzed in the same manner as in Example 9. The results are shown in Table 5 (The conversion rates are all 100%).

TABLE 5

| Substrate | Optical purity % e.e. | Steric configuration |
|---|---|---|
| $R_2$ = Methyl | 93 | (R) |
| Ethyl | 89 | (R) |
| iso-Propyl | 6 | (S) |
| iso-Butyl | 72 | (R) |

EXAMPLE 14

Process for Producing Optically Active ethyl 2-(hydroxymethyl)-3-(3,4-methylenedioxyphenyl)-propionate Each type of the Recombinant *Escherichia coli* shown in Table 6 was inoculated in 50 ml of 2×YT medium (containing 1.6% of tripeptone, 1.0% of yeast extract, and 0.5% of NaCl, pH=7.0) sterilized in a 500-ml Sakaguchi Flask, and incubated while shaking at 37° C. for 18 hours. To 1 ml of the resultant culture solution, 10 mg of ethyl 2-formyl-3-(3,4-methylenedioxyphenyl)-propionate, 1 mg of NAD (or NADP), and 10 mg of glucose were added and the mixture was stirred at 30° C. for 2 hours. After completion of the reaction, the conversion rate and optical purity of the product were analyzed in the same manner as in Example 9. The results are shown in Table 6 (The conversion rates are all 100%).

TABLE 6

| Microorganism | | Optical purity % e.e. | Steric configuration % |
|---|---|---|---|
| E. coli HB101(pNTCRG) | FERM BP-6898 | 95.7 | (R) |
| E. coli HB101(pNTDRG1) | FERM BP-08458 | 12.5 | (R) |
| E. coli HB101(pNTRGG1) | FERM BP-7858 | 78.3 | (R) |
| E. coli HB101(pNTSGG1) | FERM P-18449 | 61.3 | (R) |
| E. coli HB101(pTSBG1) | FERM BP-7119 | 42.9 | (S) |

EXAMPLE 15

Process for Producing Optically Active ethyl 2-hydroxymethylalkanoate

Each type of the Recombinant *Escherichia coli* shown in Table 7 was inoculated in 50 ml of 2×YT medium (containing 1.6% of tripeptone, 1.0% of yeast extract, and 0.5% of NaCl, pH=7.0) sterilized in a 500-ml Sakaguchi Flask, and incubated while shaking at 37° C. for 18 hours. To 1 ml of the resultant culture solution, 10 mg of ethyl type of ethyl 2-formyl alkanoate shown in Table 7, 1 mg of NAD (or NADP), and 10 mg of glucose were added and the mixture was stirred at 30° C. for 2 hours. After completion of the reaction, the conversion rate and optical purity of the product were analyzed in the same manner as in Example 12. The results are shown in Table 7 (The conversion rates are all 100%).

TABLE 7

| Microorganism | Substrate | Conversion rate % | Optical purity % e.e. | Steric configuration |
|---|---|---|---|---|
| E. coli HB101 (pNTCRG) FERM BP-6898 | Ethyl 2-formylbutyrate | 100 | 71.9 | (S) |
| | Ethyl 2-formylhexanoate | 100 | 15.4 | (S) |
| | Ethyl 2-formyloctanoate | 100 | 59.2 | (R) |
| E. coli HB101 (pNTDRG1) FERM BP-08458 | Ethyl 2-formylbutyrate | 100 | 94.2 | (S) |
| | Ethyl 2-formylhexanoate | 91 | 8.8 | (R) |
| | Ethyl 2-formyloctanoate | 93 | 0.4 | (S) |
| E. coli HB101 (pNTRGG1) FERM BP-7858 | Ethyl 2-formylbutyrate | 12.5 | — | — |
| | Ethyl 2-formylhexanoate | 30 | 94.6 | (R) |
| | Ethyl 2-formyloctanoate | 99 | 65.4 | (R) |
| E. coli HB101 (pTSBG1) FERM BP-7 119 | Ethyl 2-formylbutyrate | 77 | 62.8 | (R) |
| | Ethyl 2-formylhexanoate | 63 | 77.0 | (R) |
| | Ethyl 2-formyloctanoate | 52 | 41.9 | (R) |

EXAMPLE 16

Process for Producing ethyl (R)-2-(hydroxymethyl)-3-(3,4-methylenedioxyphenyl)-propionate Recombinant *Escherichia coli* HB101 (PNTCRG) (Accession Number: FERM BP-6898) was inoculated in 50 ml of 2× YT medium (containing 1.6% of tripeptone, 1.0% of yeast extract, and 0.5% of NaCl, pH=7.0) sterilized in a 500-ml Sakaguchi Flask and incubated while shaking at 37° C. for 18 hours. To 550 ml of the resultant culture solution, 87 g of the ethyl 2-formyl-3-(3,4-methylenedioxyphenyl)-propionate obtained in Example 1, 27.5 mg of NADP, and 89 mg of glucose were added and the mixture was stirred at 30° C. for 24 hours. After completion of the reaction, the reaction solution was extracted with toluene and the extract was concentrated to obtain 84.1 g of a blown oily substance. The chemical purity and optical purity of the product were analyzed in the same manner as in Example 9. The chemical purity was 96.5% and the optical purity was 96.4% ee. The product had an (R) configuration.

$^1$H NMR (400 Hz, CDCl$_3$) δ: 6.73-6.56 (3H, m), 5.93 (2H, s), 4.12-4.23 (2H, q), 3.76-3.64 (2H, m), 2.95-2.69 (3H, m), 1.27 (3H, t).

EXAMPLE 17

Process for Producing methyl (R)-2-(hydroxymethyl)-3-(3,4-methylenedioxyphenyl)-propionate Recombinant *Escherichia coli* HB101 (PNTCRG) (Accession Number: FERM BP-6898) was inoculated in 50 ml of 2×YT medium (containing 1.6% of tripeptone, 1.0% of yeast extract, and 0.5% of NaCl, pH=7.0) sterilized in a 500-ml Sakaguchi Flask and incubated while shaking at 37° C. for 18 hours. To 50 ml of the resultant culture solution, 1.89 g of the methyl 2-formyl-3-(3,4-methylenedioxyphenyl)-propionate obtained in Example 1, 2.5 mg of NADP, and 1.9 g of glucose were added and the reaction mixture was stirred at 30° C. for 24 hours. After completion of the reaction, the reaction solution was extracted with toluene and the extract was concentrated to obtain 1.82 g of a blown oily substance. The chemical purity and optical purity of the product were analyzed in the same manner as in Example 9. The chemical purity was 96.8% and the optical purity was 98.0% ee. The product had an (R) configuration.

$^1$H NMR (400 Hz, CDCl$_3$) δ: 6.73-6.62 (3H, m), 5.93 (2H, s), 3.77-3.67 (2H, m), 3.70 (3H, s), 2.96-2.90 (1H, m), 2.82-2.75 (2H, m).

EXAMPLE 18

Process for Producing ethyl (S)-2-(hydroxymethyl)-3-(3,4-methylenedioxybenzyl)-propionate Recombinant *Escherichia coli* HB101 (pTSBG1) (Accession Number: FERM BP-7119) was inoculated in 50 ml of 2×YT medium (containing 1.6% of tripeptone, 1.0% of yeast extract, and 0.5% of NaCl, pH=7.0) sterilized in a 500-ml Sakaguchi Flask and incubated while shaking at 37° C. for 18 hours. To 50 ml of the resultant culture solution, 0.5 g of the ethyl 2-formyl-3-(3,4-methylenedioxyphenyl)-propionate obtained in Example 1, 2.5 mg of NADP, and 0.5 g of glucose were added, and the reaction mixture was stirred at 30° C. for 24 hours. After completion of the reaction, the reaction solution was extracted with toluene and the extract was concentrated to obtain 0.49 g of a blown oily substance. The chemical purity and optical purity of the product were analyzed in the same manner as in Example 9. The chemical purity was 96.8% and the optical purity was 43.0% ee. The product had an (S) configuration.

$^1$H NMR (400 Hz, CDCl$_3$) δ: 6.73-6.56 (3H, m), 5.93 (2H, s), 4.12-4.23 (2H, q), 3.76-3.64 (2H, m), 2.95-2.69 (3H, m), 1.27 (3H, t).

EXAMPLE 19

Synthesis of ethyl (R)-2-hydroxymethylhexanoate

Recombinant *Escherichia coli* HB101 (PNTRS) (Accession Number: FERM BP-08545) was inoculated in 50 ml of 2×YT medium (containing 1.6% of tripeptone, 1.0% of yeast extract, 0.5% of NaCl, and 50 mg of zinc sulfate.7H$_2$O, pH=7.0) sterilized in a 500-ml Sakaguchi Flask and incubated while shaking at 30° C. for 40 hours. To 25 ml of the resultant culture solution, 1,000 units of glucose dehydrogenase (manufactured by Amano Enzyme Inc.), 2.5 g of ethyl 2-formylhexanoate, 3 mg of NAD, 4 g of glucose, and 50 mg of zinc sulfate.7H$_2$O were added, the culture solution was stirred at 30° C. for 24 hours while adding 2.5 M aqueous solution of sodium hydroxide dropwise to the culture solution to adjust to pH 6.5. After completion of the reaction, 100 ml of ethyl acetate was added to the reaction solution for extraction and the organic layer was distilled off under reduced pressure. Thereafter, the product was purified by silica gel chromatography to obtain an oily ethyl (R)-2-hydroxymethylhexanoate. The yield was 90% and the optical purity was 93.6% e.e. Note that analysis for optical purity was performed as follows. The product was derivatized with a HPLC labeling agent (3,5-dinitrobenzoyl chloride), and analyzed by HPLC using a Chiralcel OD-H column, 0.46×25 cm I.D. (manufactured by Daicel Chemical Industries, Ltd.).

$^1$H NMR (400 Hz, CDCl$_3$) δ: 4.13-4.24 (2H, q), 3.72-3.79 (2H, m), 2.53-2.59 (1H, m), 1.5-1.7 (2H, m), 1.24-1.37 (7H, m), 0.9 (3H, t).

EXAMPLE 20

Synthesis of ethyl (R)-2-hydroxymethylheptanoate

The titled compound was obtained as a transparent oily substance in accordance with the process of Example 19 except that ethyl 2-formylheptanoate was used in place of ethyl 2-formylhexanoate. The yield was 90% and the optical purity was 87% ee.

1H NMR (400 Hz, CDCl$_3$) δ: 4.13-4.24 (2H, q), 3.69-3.79 (2H, m), 2.53-2.59 (1H, m), 1.44-1.69 (2H, m), 1.22-1.36 (9H, m), 0.9 (3H, t).

INDUSTRIAL APPLICABILITY

According to the process of the present invention, it is possible to simply produce an optically active 3-hydroxypropionic ester derivative useful as an intermediate of a medicament from inexpensive starting materials.

The invention claimed is:
1. A process for producing an optically active 3-hydroxypropionic ester derivative represented by the formula (3):

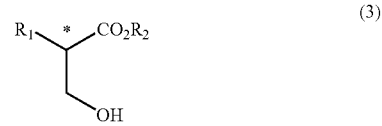

where R$_1$ represents an alkyl group having 2 to 10 carbon atoms, an optionally substituted aralkyl group having 5 to 15 carbon atoms, or an optionally substituted aryl group having 5 to 15 carbon atoms; $R_2$ represents an alkyl group having 1 to 10 carbon atoms, or an optionally substituted aralkyl group having 5 to 15 carbon atoms; and * represents an asymmetric carbon atom, characterized by subjecting a 2-formylacetic ester derivative represented by the formula (2):

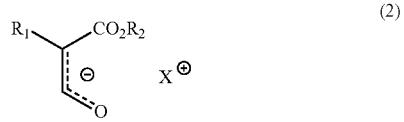

where $R_1$ and $R_2$ are the same as described above; and X represents H, Li, Na or K, to the action of an enzymatic source capable of stereoselectively reducing the formyl group thereof, wherein the R configuration of the derivative represented by the formula (3) is produced by using an enzymatic source which is derived from a microorganism of the genus of *Brettanomyces, Debaryomyces, Galactomyces, Ogataea, Pichia, Saccharomycopsis, Sporidiobolus, Sporobolomyces, Sterigmatomyces, Torulaspora, Trichosporon, Yamadazyma, Achromobacter, Cellulomonas, Devosia, Hafnia, Jensenia, Klebsiella, Micrococcus, Proteus*, or *Serratia*, and capable of R-selectively reducing the formyl group of the derivative represented by the formula (2); or the S configuration of the derivative represented by the formula (3) is produced by using an enzymatic source which is derived from an microorganism of the genus of *Cystofillobasidium, Pichia, Torulaspora, Williopsis, Devosia, Microbacterium*, or *Micrococcus* and capable of S-selectively reducing the formyl group of the derivative represented by the formula (2), and recovering the optically active 3-hydroxypropionic ester derivative represented by the formula (3) after the stereoselective reduction.

2. The process according to claim 1 wherein in the formulas (2) and (3), $R_1$ is an alkyl group having 2 to 10 carbon atoms or an optionally substituted aralkyl group having 5 to 15 carbon atoms.

3. The process according to claim 1 or 2 wherein the R configuration of the derivative represented by the formula (3) is produced by using, as the R-selective enzymatic source, an enzymatic source derived from a microorganism selected from the group consisting of *Brettanomyces anomalus, Debaryomyces nepalensis, Debaryomyces robertsiae, Galactomyces reessii, Ogataea minuta var. minuta, Pichia canadensis, Pichia silvicola, Pichia xylosa, Saccharomycopsis selenospora, Sporidiobolus johnsonii, Sporidiobolus salmonicolor, Sporobolomyces salmonicolor, Sterigmatomyces halophilus, Torulaspora delbrueckii, Trichosporon asteroids, Yamadazyma stipitis, Achromobacter xylosoxidans subsp. denitrificans, Cellulomonas fimi, Cellulomonas sp., Cellulomonas uda, Devosia riboflavina, Hafnia alvei, Jensenia canicruria, Kiebsiella planticola, Micrococcus luteus, Proteus inconstans*, and *Serratia marcescens*.

4. The process according to claim 1 or 2, wherein the R-selective enzymatic source is a cultured product of *Escherichia coli* HB101 (pNTDRG1)(FERM BP-08458), or *Escherichia coli* HB101 (pTSBG1)(FERM BP-7119); or a processed product thereof.

5. The process according to claim 1 or 2 wherein the S configuration of the derivative represented by the formula (3) is produced by using, as the S-selective enzymatic source, an enzymatic source derived from a microorganism selected from the group consisting of *Cystofillobasidium bisporidii, Pichia bispola, Torulaspora globosa, Williopsis saturnus var. mrakii, Williopsis saturnus var. saturnus, Devosia riboflavina, Microbacterium esteraromaticum*, and *Micrococcus luteus*.

6. The process according to claim 1 or 2, wherein the S-selective enzymatic source is a cultured product of *Escherichia coli* HB 101 (pNTDRG 1 )(FERM BP-08458), or *Eseherichia coli* HB101 (pTSBG1)(FERM BP-7119); or a processed product thereof.

7. A process for producing an optically active 3-hydroxypropionic ester derivative represented by the formula (3):

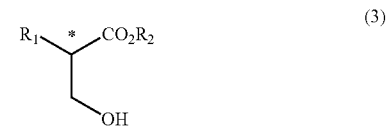

where $R_1$ represents an alkyl group having 2 to 10 carbon atoms, an optionally substituted aralkyl group having 5 to 15 carbon atoms, or an optionally substituted aryl group having 5 to 15 carbon atoms; and $R_2$ represents an alkyl group having 1 to 10 carbon atoms, or an optionally substituted aralkyl group having 5 to 15 carbon atoms; and * represents an asymmetric carbon atom, characterized by comprising the steps of:

reacting an acetic ester derivative represented by the formula (1):

where $R_1$ and $R_2$ are the same as described above with a base and a formic ester, thereby converting the acetic ester derivative into a 2-formylacetic ester derivative represented by the formula (2):

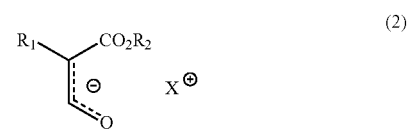

where $R_1$ and $R_2$ are the same as described above; and X represents H, Li, Na or K;

removing impurities from the reaction mixture into an organic layer formed by addition of an organic solvent and water thereto, while transferring/dissolving the derivative represented by the formula (2) into a resulting aqueous layer; and stereoselectively reducing the derivative represented by the formula (2) by use of an enzymatic source capable of stereoselectively reducing the formyl group of the derivative represented by the formula (2), thereby obtaining the optically active 3-hydroxypropionic ester derivative represented by the formula (3);

wherein the enzymatic source is derived from a microorganism belonging to the genus *Brettanomyces, Debaryomyces, Galactomyces, Ogataea, Pichia, Saccharomycopsis, Sporidiobolus, Sporobolomyces, Sterigmatomyces, Torulaspora,*

*Trichosporon, Yamadazyma, Achromobacter, Cellulomonas, Devosia, Hafnia, Jensenia, Kiebsiella, Proteus, Serratia, Cystofillobasidium, Williopsis, Microbacterium,* or *Micrococcus,* and recovering the optically active 3-hydroxypropionic ester derivative represented by the formula (3) after the stereoselective reduction.

8. The process according to claim 7 wherein, in the formulas (1), (2), and (3), $R_1$ is an alkyl group having 2 to 10 carbon atoms or an optionally substituted aralkyl group having 5 to 15 carbon atoms.

9. The process according to claim 7 or 8 wherein, in the formulas (1), (2) and (3), $R_2$ is an alkyl group having 1 to 10 carbon atoms.

10. The process according to claim 7 wherein the R configuration of the derivative represented by the formula (3) is produced by using an enzymatic source which is derived from a microorganism belonging to the genus of *Brettanomyces, Debaryomyces, Galactomyces, Ogataea, Pichia, Saccharomycopsis, Sporidiobolus, Sporobolomyces, Sterigmatomyces, Torulaspora, Trichosporon, Yamadazyma, Achromobacter, Cellulomonas, Devosia, Hafnia, Jensenia, Kiebsiella, Micrococcus, Proteus,* or *Serratia* and capable of R-selectively reducing the formyl group of the derivative represented by the formula (2).

11. The process according to claim 10 wherein the enzymatic source capable of R-selective reduction is derived from a microorganism selected from the group consisting of *Brettanomyces anomalus, Debaryomyces nepalensis, Debaryomyces robertsiae, Galactomyces reessii, Ogataea minuta var. minuta, Pichia canadensis, Pichia silvicola, Pichia xylosa, Saccharomycopsis selenospora, Sporidiobolus johnsonii, Sporidiobolus salmonicolor, Sporobolomyces salmonicolor, Sterigmatomyces halophilus, Torulaspora delbrueckii, Trichosporon asteroids, Yamadazyma stipitis, Achromobacter xylosoxidans subsp. denitrificans, Cellulomonas fimi, Cellulomonas sp., Cellulomonas uda, Devosia riboflavina, Hafnia alvei, Jensenia canicruria, Kiebsiella planticola, Micrococcus luteus, Proteus inconstans,* and *Serratia marcescens.*

12. The process according to claim 11 wherein the enzymatic source capable of R-selective reduction is a culture product of *Escherichia coli* HB 101 (pNTDRG1)(FERM BP-08458), or *Escherichia coli* HB101 (pTSBG1)(FERM BP-7119); or a processed product thereof.

13. The process according to claim 7 wherein the S configuration of the derivative represented by the formula (3) is produced by using an enzymatic source which is derived from a microorganism belonging to the genus of *Cystofillobasidium, Pichia, Torulaspora, Williopsis, Devosia, Microbacterium,* or *Micrococcus* and capable of S-selectively reducing the formyl group of the derivative represented by the formula (2).

14. The process according to claim 13 wherein the enzymatic source capable of S-selectively reducing the formyl group of the derivative represented by the formula (2) is derived from a microorganism selected from the group consisting of *Cystofillobasidium bisporidii, Pichia bispola, Torulaspora globosa, Williopsis saturnus var. mrakii, Williopsis saturnus var. saturnus, Devosia riboflavina, Microbacterium esteraromaticum* and *Micrococcus luteus.*

15. The process according to claim 13 or 14 wherein the enzymatic source capable of S-selectively reducing the formyl group of the derivative represented by the formula (2) is a cultured product of *Escherichia coli* HB 101 (pNTDRG1) (FERM BP-08458), or *Escherichia coli* HB101 (pTSBG1) (FERM BP-7119); or a processed product thereof.

\* \* \* \* \*